United States Patent
Abraham-Fuchs et al.

[11] Patent Number: 5,871,627
[45] Date of Patent: Feb. 16, 1999

[54] FLOW-THROUGH MEASUREMENT CELL FOR EXTRACORPOREAL MEASUREMENT OF BLOOD PARAMETERS

[75] Inventors: Klaus Abraham-Fuchs, Erlangen; Walter Gumbrecht, Herzogenaurach; Christofer Hierold, Munich, all of Germany

[73] Assignee: Siemens Aktiengesellschaft, Munich, Germany

[21] Appl. No.: 862,364

[22] Filed: May 23, 1997

[30] Foreign Application Priority Data

May 31, 1996 [DE] Germany ............ 196 22 079.3
Apr. 4, 1997 [EP] European Pat. Off. ............ 97105614

[51] Int. Cl.⁶ .................................................. G01N 27/26

[52] U.S. Cl. ............................ 204/400; 204/409; 600/488

[58] Field of Search .................... 356/79; 73/700, 73/863.51, 756, 40.5 A; 7/754, 426, 863.41, 485, 52, 40, 40.5 R; 204/400, 409; 205/792; 600/345, 488

Primary Examiner—Robert Warden
Assistant Examiner—Alex Noguerola
Attorney, Agent, or Firm—Hill & Simpson

[57] ABSTRACT

A flow-through cell for extra-corporeal measurement of blood parameters has a pressure sensor arranged in a measurement chamber. The pressure sensor has an active pressure sensor part and an inactive pressure sensor part. The inactive pressure sensor part is constructed identically to the active pressure sensor part, and is insulated from the pressure prevailing in the measurement chamber by a rigid covering. The active and inactive sensor parts produce respective electrical signals which are subject to the same disturbing influences, so that by subtracting the signal of the inactive sensor part from the signal of the active sensor part, a measured value free of disturbing influences is obtained.

12 Claims, 1 Drawing Sheet

FLOW-THROUGH MEASUREMENT CELL FOR EXTRACORPOREAL MEASUREMENT OF BLOOD PARAMETERS

BACKGROUND OF THE INVENTION

1. Field of the Invention

The present invention is directed to a flow-through measurement cell for the extracorporeal measurement of blood parameters, of the type having a pressure sensor arranged in a measurement chamber.

2. Description of the Prior Art

A flow-through measurement cell of the general type described above is known from PCT publication WO 92/05449. This flow-through measurement cell has a first measurement chamber with several electrochemical sensors arranged therein. An inlet opening of the first measurement chamber is connected with a switching unit via a liquid connection line. A liquid conveyor apparatus is connected to an outlet opening of the first measurement chamber. Dependent on the switch position of the switching unit, liquid being measured, rinse solution or calibration solution can be suctioned through the measurement chamber by means of the liquid conveyor apparatus and then conveyed into a waste receptacle. Separately from the first measurement chamber, a pressure sensor is arranged in a second measurement chamber of the flow-through measurement cell. The second measurement chamber is connected with the switching unit via an additional liquid connection line. In the switching unit, in the switching states "ready" and "measure" a connection is created to a measurement line, so that in these switch positions a continuous pressure measurement can ensue.

An additional flow-through measurement cell for extracorporeal measurement of several electrochemically measured blood parameters, such as e.g. pH concentration, $pO^2$ concentration, $pCO_2$ value and electrolyte concentration, is described in U.S. Pat. No. 4,841,974. It is connected to an arterial permanent catheter. The sensors are arranged in the flow-through measurement cell in a wall of a measurement duct. The sensors themselves are fashioned as ion-sensitive field-effect transistors that are jointly integrated on a silicon chip. A membrane, which forms a boundary surface to the measurement medium, i.e. to the removed blood, thereby serves as a control electrode. An allocated evaluation electronics is likewise integrated on the chip, and forms a structural unit with the sensors. The construction of the chip is also specified in the article by W. Gumbrecht, D. Peters, W. Schelter, W. Erhardt, J. Henkel, J. Steil and U. Sykora: "Integrated $pO^2$, $pCO_2$, pH Sensor System for Online Blood Monitoring," Sensors and Actuators B, 18–19 (1994), pp. 704–708.

In European Application 0 714 017, silicon thin film pressure sensors are specified that can be manufactured in a manner compatible with processes that are standard in CMOS technology. As used herein, "compatible with CMOS manufacturing processes" means that the additional process steps required in the manufacture of the sensor can be incorporated into standard CMOS process steps, and do not disturb them. This technology is also known as surface micromechanics technology. In addition to the pressure sensor, further electronic circuits are monolithically integrated on the same chip.

In a different type of technology also used for surface micromechanics, known as bulk micromechanics technology, the sensors are etched considerably deeper into the silicon substrate material than in the surface micromechanics technology.

SUMMARY OF THE INVENTION

An object of the present invention is to provide a compact and robust flow-through measurement cell for extracorporeal measurement of blood parameters, with which a blood monitoring system can be constructed that is easy to operate and is not sensitive to disturbances.

This object is achieved in a flow-through cell having a pressure sensor wherein the pressure sensor has an active pressure sensor part and an inactive pressure sensor part, and wherein the construction of the inactive pressure sensor part is identical to that of the active pressure sensor part, and wherein the inactive pressure sensor part is insulated from the pressure that prevails in the measurement channel by means of a rigid covering. The output signal of the identically constructed but inactive pressure sensor part is thus subject to, in the same way as the active sensor which serves as the blood pressure sensor, by further influences, such as e.g. temperature and voltages in the substrate material, as well as by variabilities caused during manufacture, and can be used for the correction of these disturbing influences.

In an embodiment, at least one electrochemical sensor is additionally arranged in the measurement chamber. The arrangement of one or more electrochemical sensors with the pressure sensor in one housing simplifies, the operation of the sensors, and makes the flow-through measurement cell insensitive to disturbances. Moreover, the possibility is thereby created of additionally arranging evaluation electronics in the same housing, in which all sensors for the determination of blood parameters are then housed.

In a further embodiment, a first supply channel is connected with a first end of the measurement chamber, the first supply channel being provided for connection to a catheter, and the pressure sensor is arranged at the first end of the measurement channel. The arrangement of the pressure sensor close to the patient enables a substantially undamped measurement of the arterial blood pressure.

In a further embodiment, a second supply channel is connected with a second end of the measurement chamber, the second supply channel being provided for the connection of a liquid conveyance apparatus. The first supply channel has cross-section which is larger than the cross-section of the second supply channel. For measurement accuracy, the blood sample to be analyzed must be conveyed through the entire measurement channel, and then further into the second supply channel. The smaller cross-section of the second supply channel keeps the overall volume required for the measurement of the blood parameters in the flow-through measurement cell as small as possible.

In another embodiment, an external pressure sensor is arranged outside the measurement chamber for the measurement of external air pressure prevailing outside the measurement channel. The external pressure sensor measures the external air pressure, which can then be subtracted from the pressure measured by the pressure sensor which interacts with the arterial blood column. Since the pressure sensor arranged in the measurement chamber measures a sum of ambient air pressure and arterial blood pressure, the arterial blood pressure can be determined by means of subtraction. The communication of the external pressure sensor with the surrounding air pressure can be produced by means of a bore in the housing. This bore can be sealed with a membrane impermeable to moisture that transmits the air pressure but prevents penetration of splashed water, water vapor in the air or the like.

The external pressure sensor also can have an active and an inactive external pressure sensor parts, with the inactive external pressure sensor part being of identical construction to the active external pressure sensor part, and the inactive external pressure sensor part being insulated from the external air pressure by means of a rigid covering. In this way, the measurement values of the external pressure sensor can also be made free of disturbing influences.

An economical and compact flow-through measurement cell can be constructed according to a further embodiment, by connecting the pressure sensor, or pressure sensors, with signal processing components, and monolithically integrating the signal processing components with the pressure sensor or pressure sensors on one chip. The signal processing components can be manufactured e.g. in CMOS technology, and the pressure sensors can be manufactured with CMOS-compatible surface micromechanics technology.

A particularly compact flow-through measurement cell, requiring only a small blood volume for measurement, can then be constructed by, according to a further embodiment, integrating all the sensors monolithically integrated on one chip. Using CMOS-compatible process steps, currently available surface micromechanics technology allows the monolithic integration of all sensors.

In a further embodiment, the signal processing components allocated to the sensors are also monolithically integrated on the chip. The susceptibility of the flow-through measurement cell with the sensors to disturbances is thereby further reduced, and the measurement signal can thereby be converted into a disturbance-insensitive form for transmission.

DESCRIPTION OF THE PREFERRED EMBODIMENTS

Figure 1:
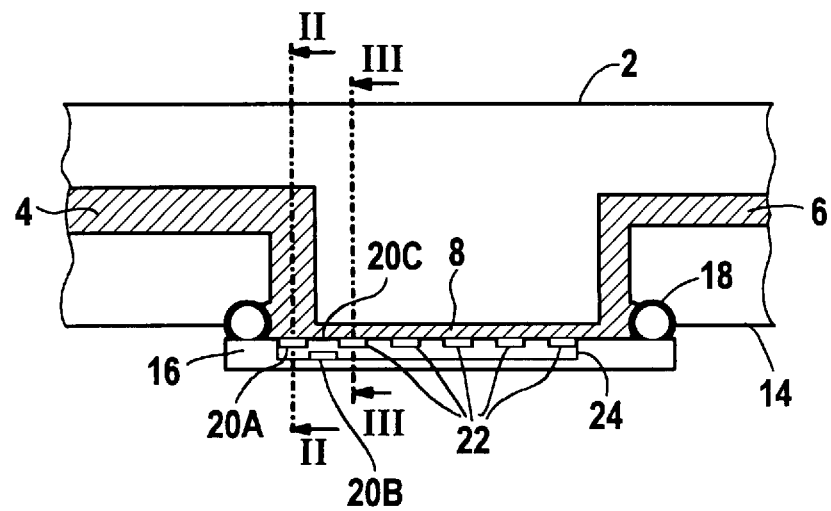
FIG. 1 shows, in a schematic sectional representation, a two-way flow-through measurement cell with chemosensors and a pressure sensor, constructed in accordance with the principles of the present invention.

The two-way flow-through measurement cell shown in FIG. 1 is used for the extra-corporeal measurement of chemical and physical blood parameters. Supply channels 4 and 6 are made in a support block 2, which channels lead respectively opposite to ends of a measurement chamber fashioned as a measurement channel 8. The supply channels 4, 6 are each connected at their other end (not shown) with connection means for tube lines, or catheters. As connection means, fixed or detachable connection elements standardly used in medical technology may be used, however, these are not shown in FIG. 1. The first supply channel 4 is provided for the connection of the two-way flow-through measurement cell to an arterial catheter. The second supply channel 6 is provided, among other things, for the connection of the two-way flow-through measurement cell to a pump, in order to convey a blood sample from the artery to the measurement channel 8. The supply channels 4 and 6 first extend in the longitudinal direction into the support block 2; they then turn toward a side surface 14 and open there into the measurement channel 8. The supply channels 4 and 6 at that location are at a right angle to the side surface 14. The cross-section of the supply channel 4 is formed large enough that the arterial blood pressure can be conducted almost undamped to the measurement channel 8. In contrast, the volume of the measurement channel 8 and the cross-section of the second supply channel 6 are formed as small as possible, in order to keep the required overall probe volume in the flow-through measurement cell as small as possible. A wall of the measurement channel 8 is formed by a silicon semiconductor chip 16 that is arranged at a distance from the side surface 14 that determines the height of the measurement channel 8. A circumferential sealing ring 18 seals the region between the semiconductor chip 16 and the support block 2. The sealing ring 18 thus surround the measurement channel 8 laterally, as well as the openings of the supply channels 4 and 6 in the side surface 14.

On the semiconductor chip 16, all sensors are produced in integrated fashion on the side that faces the measurement channel 8. A pressure sensor is arranged at the end of the supply channel 4. Additional sensors 22 are arranged on the semiconductor chip 16 along the length of the measurement channel 8 for the measurement of further blood parameters, such as e.g. blood gas values, electrolyte concentrations and metabolite concentrations; temperature sensors and, if necessary, flow sensors are also arranged there. The electrochemical sensors are constructed in thin film and thick film technique, and the pressure sensor is constructed in surface micromechanics technology. A signal processing circuit 24 for the sensors is likewise integrated (preferably in CMOS technology) on the semiconductor chip 16. The signal processing circuit 24 includes analog-digital converters that digitize the measurement signal in order to enable disturbance-insensitive signal transmission from the chip 16 to further electronic evaluation circuits.

The pressure sensor includes an active pressure sensor part 20A, which emits a measurement signal that depends on the pressure, and also an identically constructed inactive pressure sensor part 20B, which is insulated from the pressure prevailing in the measurement duct 8 by means of a rigid covering 20C. The output signal of the identically constructed but inactive pressure sensor part 20B is determined by disturbing influences (e.g. temperature, warping in the support material, and manufacturing-related tolerances) to the same extent as the output signal of the active pressure sensor part 20A, and can be used for the correction of these disturbing influences.

Figure 2:
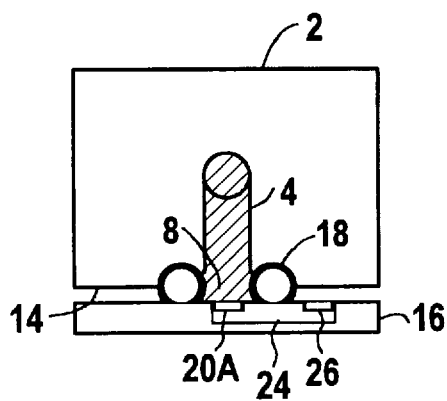
FIG. 2 shows a sectional representation of the two-way flow-through measurement cell according to FIG. 1, in a plane II.

FIG. 2 shows a sectional representation (along a sectional plane designated II in FIG. 1) of the first supply channel 4, in which the active pressure sensor part 20A is arranged on the semiconductor chip 16. In addition to the pressure sensor part 20A, another external pressure sensor 26 is integrated on the semiconductor chip 16 for the measurement of external air pressure prevailing outside the measurement channel 8. Like the pressure sensor in the measurement channel 8, the external pressure sensor 26 has an active external pressure sensor part and an inactive external pressure sensor part for the compensation of disturbing influences. The external pressure sensor 26 can be separated from the surrounding environment by a membrane that is impermeable to moisture but transmits air pressure.

The blood pressure value of the patient is obtained in principle by first forming the pressure measurement values, made free of disturbing influences, from the active pressure sensor part 20A and of the external pressure sensor 26. The pressure measurement values free of disturbing influences result e.g. from a subtraction, whereby the value of the inactive pressure sensor part 20B is subtracted from the measurement value of the active pressure sensor part 20A. The blood pressure value itself is obtained by means of a further subtraction, by subtracting the external atmospheric pressure (made free of disturbing influences if necessary) from the blood pressure measurement value (made free of disturbing influences if necessary). At least one part of this signal processing is carried out by electronic signal processing circuits integrated on the semiconductor chip 16.

Figure 3:
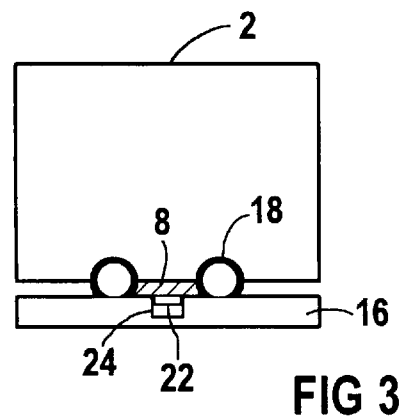
FIG. 3 shows a sectional representation of the two-way flow-through measurement cell according to FIG. 1 in the plane III.

The sectional representation in FIG. 3 along the sectional plane III shows in particular the cross-section of the measurement duct 8, determined substantially by the distance of the semiconductor chip 16 from the support block 2 and the size of the additional sensors 22.

Figure 4:
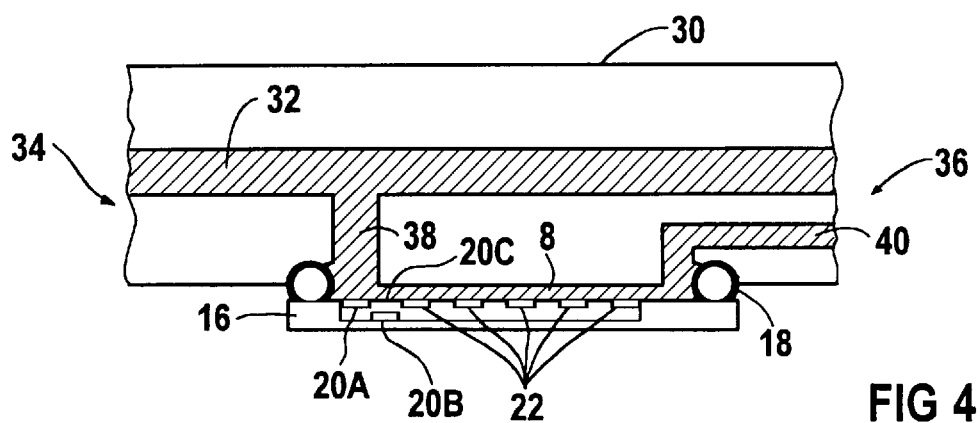
FIG. 4 shows a schematic sectional representation of a three-way flow-through measurement cell with chemosensors and a pressure sensor constructed in accordance with the principles of the present invention.

The three-way flow-through measurement cell shown in section in FIG. 4 uses the same semiconductor chip 16 as the two-way flow-through cell according to FIG. 1; only the liquid-conducting ducts have been changed. A flow-through channel 32 that runs in a straight line and has a large cross-section is worked into a support block 30, which opens into the opposed left and right sides 34 and 36. The opening in the left side 34 is formed for the connection of the arterial permanent catheter, while the opening in the right side 36 is provided for the connection of a supply container for an infusion solution with an associated conveyor apparatus.

A branch 38 leads from the flow-through channel 32 to the measurement channel 8. The cross-section of the flow-through channel 32 is at least as large as the cross-section of the branch 38, and the cross-section of the branch 38 is sufficiently large so that the arterial blood pressure to be measured can be conducted undamped up to the pressure sensor 20. The part of the flow-through channel 32 from the left side 34 up to the opening of the branch 38 and then up to the measurement channel 8 corresponds to the first supply channel 4 of the two-way flow-through measurement cell in FIG. 1. A connection channel 40 is guided to the other end of the measurement channel 8. The connection channel 40 likewise opens into the right side 36. The connection channel 40 is provided for the connection of a blood conveyor apparatus, with which blood samples can be removed and pumped to the sensors 20A and 22 in the measurement channel 8; it corresponds to the second supply channel 6 of the two-way flow-through measurement cell in FIG. 1.

Although modifications and changes may be suggested by those skilled in the art, it is the intention of the inventors to embody within the patent warranted hereon all changes and modifications as reasonably and properly come within the scope of their contribution to the art.

We claim as our invention:

1. A flow-through measurement cell for extracorporeally measuring blood parameters, comprising:
    a measurement chamber having a pressure prevailing therein;
    a pressure sensor disposed in said measurement chamber, said pressure sensor comprising an active sensor part and an inactive pressure sensor part constructed identically to said active pressure sensor part, said active pressure sensor part being exposed to said pressure prevailing in said measurement chamber; and
    a rigid covering over said inactive pressure sensor part for insulating said inactive pressure sensor part from said pressure prevailing in said measurement chamber.

2. A flow-through measurement cell as claimed in claim 1 further comprising at least one electrochemical sensor disposed in said measurement chamber.

3. A flow-through measurement cell as claimed in claim 1 wherein said measurement chamber has opposite first and second ends, and said flow-through measurement cell further comprising a first supply channel connected at said first end of said measurement chamber and adapted for connection to a catheter, and said pressure sensor being disposed at said first end of said measurement chamber.

4. A flow-through measurement cell as claimed in claim 3 further comprising a second supply channel connected at said second end of said measurement chamber and adapted for connection to a liquid conveyor apparatus, said first supply channel having a first cross-section and said second supply channel having a second cross-section, said first cross-section being larger than said second cross-section.

5. A flow-through measurement cell as claimed in claim 1 further comprising an external pressure sensor disposed outside of said measurement chamber for measuring external air pressure prevailing outside of said measurement chamber.

6. A flow-through measurement cell as claimed in claim 5 wherein said external pressure sensor comprises an active external pressure sensor part exposed to said external air pressure and an inactive external pressure sensor part constructed identically to said active external pressure sensor part, and a rigid covering over said inactive external pressure sensor part insulating said inactive external pressure sensor part from said external air pressure.

7. A flow-through measurement cell as claimed in claim 6 further comprising a plurality of signal processing components electrically connected to said external pressure sensor and monolithically integrated on a single chip with said external pressure sensor also being monolithically integrated on said single chip.

8. A flow-through meausrement cell as claimed in claim 6 wherein said pressurre sensor in said measurement chamber and said external pressure sensor are monolithically integrated on a single chip.

9. A flow-through measurement cell as claimed in claim 8 further comprising a plurality of signal processing components for said pressure sensor in said measurement chamber and said external pressure sensor also monolithically integrated on said single chip.

10. A flow-through measurement cell as claimed in claim 9 wherein said single chip comprises a silicon chip.

11. A flow-through measurement cell as claimed in claim 1 further comprising signal processing components electrically connected to said pressure sensor, and monolithically integrated on a single chip with said pressure sensor.

12. A flow-through measurement cell as claimed in claim 11 wherein said single chip comprises a silicon chip.

* * * * *

UNITED STATES PATENT AND TRADEMARK OFFICE
CERTIFICATE OF CORRECTION

PATENT NO. : 5,871,627
DATED : February 16, 1999
INVENTOR(S) : Abraham-Fuchs et al.

It is certified that error appears in the above-identified patent and that said Letters Patent is hereby corrected as shown below:

Title page,
Item [56] insert the following:

U.S. PATENT DOCUMENTS

| Patent number | Issue Date | Patentee |
|---|---|---|
| 5631428 | 5/20/97 | Catanscu et al. |
| 5086777 | 2/11/92 | Hishii |
| 4841974 | 6/27/89 | Gumbrecht et al. |
| 4625560 | 12/2/86 | Sanders |
| 4608996 | 9/2/86 | Brown |
| 4554927 | 11/26/85 | Fussell |

FOREIGN PATENT APPLICATION

| Document Number | Publication Date | Country or Patent Office |
|---|---|---|
| OS 43 06 184 | 9/1/94 | Germany |
| 0 240 735 | 10/14/87 | Europe |
| WO 92/05449 | 4/2/92 | PCT |

Signed and Sealed this

Sixth Day of November, 2001

Attest:

NICHOLAS P. GODICI
*Attesting Officer*        *Acting Director of the United States Patent and Trademark Office*